United States Patent
Lundmark et al.

(12) 
(10) Patent No.: US 6,743,434 B1
(45) Date of Patent: Jun. 1, 2004

(54) CARBONIC EMULSION SKIN CARE COMPOSITIONS AND METHOD FOR REMOVING CHEMICALLY BOUND RESIDUES AND MINERAL DEPOSITS FROM HAIR

(76) Inventors: Larry D. Lundmark, 7540 Orchid La. N., Maple Grove, MN (US) 55311; Wallace R. Hlavac, 1201 Yale Pl., Minneapolis, MN (US) 55403

( * ) Notice: Subject to any disclaimer, the term of this patent is extended or adjusted under 35 U.S.C. 154(b) by 36 days.

(21) Appl. No.: 10/145,511

(22) Filed: May 14, 2002

(51) Int. Cl.[7] ............................. A61K 7/00; A61K 7/06; A61K 7/08; A61K 7/075; A61K 31/415
(52) U.S. Cl. .................... 424/401; 424/70.1; 424/70.22; 424/70.24; 424/400; 514/390
(58) Field of Search .............................. 424/70.1, 400, 424/401, 70.22, 70.24; 514/390

(56) References Cited

U.S. PATENT DOCUMENTS

| | | |
|---|---|---|
| 3,998,761 A | 12/1976 | Gary et al. |
| 4,412,026 A | 10/1983 | Collins |
| 4,581,229 A | 4/1986 | Petrow |
| 5,041,285 A | 8/1991 | Lundmark |
| 5,112,359 A | 5/1992 | Murphy et al. |
| 5,635,167 A | 6/1997 | Said et al. |
| 5,804,172 A | 9/1998 | Ault |
| 5,948,416 A | 9/1999 | Wagner et al. |
| 6,153,208 A * | 11/2000 | McAtee et al. ............. 424/402 |
| 6,365,143 B1 | 4/2002 | Lundmark et al. |

OTHER PUBLICATIONS

Effect of Carbon Dioxide—Enriched Water and Fresh Water on the Cutaneous Microcirculation and Oxygen Tension in the Skin of Foot Hartmann et. al., Angiology, vol. 48, pp. 337–343 (1997).

G. Ramachandra Bhat, et. al., *J.Soc. Cosmet. Chem.*, 30, 1–8 (Jan./Feb. 1979).

* cited by examiner

*Primary Examiner*—Shelley A. Dodson
(74) *Attorney, Agent, or Firm*—Forrest L. Collins

(57) ABSTRACT

The invention, in part, relates to skin care or hair care compositions containing a source of carbon dioxide. The carbon dioxide is conveniently entrained in a gel-network, or liquid crystalline phase, immediately prior to skin or hair application. A substantial portion of the carbon dioxide will be lost from the product upon application to the skin or hair. However, a sufficient amount of carbon dioxide will remain in the product to stimulate oxygen flow to the outer layers of the skin with the apparent retardation of skin aging. The present invention also relates to the field of hair treatment and particularly to the removal of chemically bound residues and mineral deposits from hair. Hair may act as a sink for environmental minerals and heavy metals. In addition to undesirable changes in color and appearance, environmental minerals may have an adverse effect on chemical hair treatments. Mineral deposits in tap water may strip away highlights, darkening hair to a brassier hue. In both skin and hair care products, the liberated carbon dioxide also functions to facilitate the delivery of active or functional substances to keratinous substrates, such as skin and hair.

23 Claims, No Drawings

CARBONIC EMULSION SKIN CARE COMPOSITIONS AND METHOD FOR REMOVING CHEMICALLY BOUND RESIDUES AND MINERAL DEPOSITS FROM HAIR

BACKGROUND OF THE INVENTION

1. Field of the Invention

The present invention relates to the field of skin care, and the apparent retardation of skin aging. The present invention also relates to the field of hair treatment and particularly to the removal of chemically bound residues and mineral deposits from hair. Hair may act as a sink for environmental minerals and heavy metals. In addition to undesirable changes in color and appearance, environmental minerals may have an adverse effect on chemical hair treatments. Mineral deposits in tap water may strip away highlights, darkening hair color to a brassier hue.

2. Description of the Art Practices

U.S. Pat. No. 5,041,285 issued to Lundmark on Aug. 20, 1991 describes a composition containing allantoin, panthenol, and a monohydric alcohol. The Lundmark patent describes a substantially homogeneous product obtained by: dispersing panthenol in a monohydric alcohol at a temperature above the melting point of the panthenol to obtain a liquid melt; and dispersing allantoin in the liquid melt at a temperature above the point at which the liquid melt is in the liquid phase. The product described in the Lundmark patent is for the treatment of keratinous substrates, including the treatment of hair.

The phenomenon of blonde hair acquiring a green tint when exposed to swimming pool water containing copper has been attributed to copper mineral absorption by hair. Such absorption occurs when copper is in the form of a weak complex of copper salts. Subsequent shampooing with a conventional composition cannot strip the green color. (Reference: G. Ramachandra Bhat, et. al., *J. Soc. Cosmet. Chem.*, 30, 1–8 (January/February 1979).

Previous attempts to develop compositions for the removal of minerals from human hair have utilized high concentrations of known chelating agents, extended contact times and processes which require the application of heat. In addition, special packaging may be required to prevent decomposition in the presence of air. For example, Ault in U.S. Pat. No. 5,804,172 issued Sep. 8, 1998 discloses a composition for use in removal of minerals from hair which comprises the combination of an acidifying agent, a reducing agent, a chelating agent, a gelling agent and water. A synergistic combination of chelating agents is stated to be disclosed in the Ault patent. Also disclosed in the Ault patent is a process for packaging the compositions and a method for removal of mineral residues from hair by the use of such compositions. The method disclosed in the Ault patent for the removal of mineral residues from hair may take up to 45 minutes for the removal of iron from hair. It is also stated in the Ault patent that the process requires the application of heat and an airtight container to prevent oxidation that would negate the usefulness of the invention.

U.S. Pat. No. 5,635,167 to Said, et al., issued Jun. 3, 1997 discloses a process for the removal of exogenous metal ions attached to human hair or keratin fiber which include the steps of contacting at least one chelating agent to the human hair or keratin fiber, the chelating agent selected from the group consisting of amino acid-type, polyphosphate-type and phosphonate-type agents, maintaining contact with the chelating agent and the human hair or keratin fiber for a period of time sufficient to permit the chelating agent to complex with the exogenous minerals, thereby removing at least a portion of the attached minerals, and rinsing the chelating agent.

The process of the Said, et al., patent is enhanced with the pH adjusted to a range of between 4 to 9, preferably 5 to 8. The chelating agent of the Said, et al., patent is added at a concentration of 4% by weight to 25% by weight, preferably 5 to 20% by weight. In a preferred case, the chelating agent is selected from the group consisting of a salt of ethylenediamine-tetraacetic acid, a salt of hydroxyethylethylenediaminetriacetic acid, a salt of diethylenetriaminepentaacetic acid, a salt of nitrilotriacetic acid and a salt of tripolyphosphate, preferably the sodium salt. The Said, et al., patent teaches high concentrations of polyphosphate or phosphonate which may be irritating to the scalp of certain sensitive individuals and may limit the utility of the proposed invention for use in low irritation shampoo compositions.

Gary, et al., in U.S. Pat. No. 3,998,761 issued Dec. 21, 1976 discloses a shampoo composition suitable for conditioning hair. The compositions of the Gary, et al., patent comprise at least one detergent and a waste liquid beer sludge concentrate distributed in an aqueous medium. The beer solids are stated to be, in the Gary, et al., patent composition at from about 4% to 20% by weight based on the total weight of the shampoo composition and wherein said detergent comprises about 10 to 20% based on the total weight of the composition. The compositions of the Gary, et al., patent may contain minor amounts of proteins.

U.S. Pat. No. 5,948,416 issued to Wagner, et al., on Sep. 7, 1999 relates to leave on, skin care compositions, comprising: (A) from about 0.001% to about 20% of an active ingredient, (B) from about 1% to about 20% of a stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, and mixtures thereof, having a melting point of at least about 45 degree C.; and (C) from about 0.05% to about 10% of a hydrophilic surfactant selected from the group consisting of anionic surfactants, cationic surfactants, zwitterionic surfactants, and mixtures thereof, and (D) from about 25% to about 98.949% water. These compositions of the Wagner, et al., patent are stated to be useful for delivering a wide variety of active ingredients to the skin.

U.S. Pat. No. 4,581,229 issued to Petrow on Apr. 8, 1986 discloses a hair treating solution and method which is stated to provide for improving hair quality and aiding in removal of inorganic substances from hair. The Petrow patent states that metals such as copper, iron, manganese, nickel and the like, if attached to hair after swimming or other hair-exposure thereto, can be removed by the use of a soluble lanthanum salt in a simple rinsing method.

The coloring of hair to a desired shade and having the hair retain the desired shade is quite important to consumers as set out in U.S. Pat. No. 5,112,359 Murphy, et al., issued May 12, 1992. The Murphy, et al., patent discloses certain dispersant free substituted diaminoanthraquinone colorants stated to be useful in hair dye compositions to more intensely color hair. The Murphy, et al., patent states that coloring kits, mousses, gels, and aerosols may contain the compositions disclosed therein.

Cationic polymers are used in shampoos and conditioners to facilitate combability and to make the hair feel softer and smoother to the touch. Cationic surfactants are positively charged molecules that have an affinity for negatively charged sites on the hair. When used repeatedly, an excess of cationic polymer may buildup on the hair shaft, resulting in dull, lifeless hair. Compositions for the removal of minerals from human hair do not address the problem of cationic polymeric buildup on the hair shaft.

The immersion of the skin in carbon dioxide enriched water has been shown to increase blood flow and oxygen delivery to the skin, Hartmann et. al., Angiology, vol. 48, pp. 337–43 (1997).

U.S. Pat. No. 4,412,026 issued to Collins Oct. 25, 1983 discusses polymeric compositions. The Collins patent in particular, describes the homopolymeric salt of 2-acrylamido-2-methylpropanesulfonic acid in an amount sufficient to thicken the compositions disclosed therein.

Throughout the specification and claims, percentages and ratios are by weight, and temperatures are in degrees Celsius, unless otherwise indicated. To the extent that any of the references cited herein are applicable, they are hereby specifically incorporated by reference. Ranges and ratios given herein may be combined.

SUMMARY OF THE INVENTION

The present invention describes a composition suitable for conditioning a keratinous substrate comprising:
(a) panthenol;
(b) citric acid;
(c) water; and,
(d) a water-soluble source of bicarbonate.

A further aspect of the present invention is a composition that is a two part composition suitable for conditioning a keratinous substrate comprising:
(a) a first mixture comprising water and citric acid; and,
(b) a second mixture comprising panthenol and, a water-soluble source of bicarbonate.

A further aspect of the present invention is a composition suitable for conditioning a keratinous substrate comprising:
(a) panthenol;
(b) citric acid;
(c) water;
(d) a water-soluble source of bicarbonate; and,
(e) a member selected from the group consisting of a water-insoluble linear alcohol and a fatty acid ester and mixtures thereof.

Further disclosed herein is a composition suitable for conditioning a keratinous substrate comprising:
(a) panthenol;
(b) citric acid;
(c) water;
(d) a water-soluble source of bicarbonate; and,
(e) a quaternary compound.

Yet a further aspect of the present invention is a two part composition suitable for conditioning a keratinous substrate comprising:
(a) a first mixture comprising water and a source of a homopolymeric salt of 2-acrylamido-2-methylpropanesulfonic acid; and,
(b) a second mixture comprising panthenol and, a water-soluble source of bicarbonate.

Yet a further aspect of the present invention is a method for treating a keratinous substrate such as skin or hair with the foregoing compositions.

DETAILED DESCRIPTION OF THE INVENTION

For the purposes of promoting an understanding of the principles of the invention, reference will now be made to the preferred embodiment. No limitation of the scope of the invention is thereby intended for further applications of the principles of the invention, which would normally occur, or be contemplated by one skilled in the art, to which the invention relates.

The first aspect of the invention, in part, relates to stable, skin care or hair care compositions containing a source of carbon dioxide. The carbon dioxide is conveniently entrained in a gel network "liquid crystalline" phase, immediately prior to use upon the skin or hair. Without being limited by theory, it is believed that the aqueous phase of these compositions contain both free water and associated water which is believed to be bound as part of a gel network or liquid crystalline phase. A substantial portion of the carbon dioxide will be lost from the product upon application to the skin or hair. However, a sufficient amount of carbon dioxide may remain in the product to stimulate the skin and help promote oxygen flow to the outer layers of the skin. In hair care products, the carbon dioxide also functions to facilitate the penetration of active substances into the hair shaft. These compositions are useful for delivering a wide variety of functional ingredients to the skin and hair.

When sodium bicarbonate (baking soda) is dissolved in water and combined with an acidic solution (e.g. citric acid), a "neutralization" reaction occurs which liberates carbon dioxide gas. In aqueous solution, sodium bicarbonate is transformed into sodium carbonate and carbon dioxide. Sodium carbonate is also decomposed by acids with effervescence. The products of the present invention permit the incorporation of carbon dioxide into a "semi-stable" liquid crystal or gel network emulsion phase for subsequent delivery to skin or hair after application to a keratinous substrate.

Emulsions are multi-phase dispersions which are typically oil-in-water (O/W), water-in-oil (W/O) or multiple phase (W/O/W) or (O/W/O). The introduction of a gaseous phase into an emulsion vehicle adds another degree of complexity, with gas bubbles coalescing and dissipating out of the multi-phase dispersion with time.

The emulsions of the present invention are multi-phase dispersions consisting of carbon dioxide gas, an oil phase and a water phase. The emulsions of the present invention may be formed by combining an alkaline sodium bicarbonate emulsion with an acidic vehicle, followed by mixing and subsequent gas phase effervescence.

Skin cells utilize oxygen to facilitate the production of extracellular matrix substances which is essential for maintaining healthy looking skin. As humans age, oxygen levels in the skin tend to decrease. Increased blood flow to the skin tends to increase skin oxygen levels. Immersion of the skin in carbon dioxide enriched water has been shown to increase blood flow and oxygen delivery to the skin (Ref. Hartmann et. al., Angiology, vol. 48, pp. 337–43 (1997)). It should be noted that oxygen does not increase blood flow to the skin when administered topically because oxygen is not a vasodilator. The delivery of carbon dioxide to the skin via an emulsion vehicle would therefore be a desirable "anti-aging" innovation.

Hair is an assembly of fibers that contain proteins, which may bind minerals by both ionic bonds and covalent bonds. In addition to undesirable changes in color and appearance, environmental minerals may have an adverse effect on chemical hair treatments. Mineral deposits in tap water may strip away highlights, darkening hair color to a brassier hue.

The phenomenon of blonde hair acquiring a green tint when exposed to swimming pool water containing copper has been attributed to copper mineral absorption by hair. Such absorption occurs when copper is in the form of a weak complex of copper salts. Subsequent shampooing with a conventional composition cannot strip the green color.

The green hair effect is associated with conditions which stress the hair, e.g. chlorine in a swimming pool, and the presence of dissolved copper salts. Thus, a hair conditioner, which simultaneously facilitates the removal of bound environmental minerals and conditions the hair, is a desirable consumer innovation.

Cationic polymers are used in shampoos and conditioners to enhance combability and to make the hair feel softer and smoother to the touch. Cationic surfactants are positively charged molecules that have an affinity for negatively charged sites on the hair. When used repeatedly, an excess of cationic polymer may buildup on the hair shaft, resulting in dull, lifeless hair. Compositions for the removal of minerals from human hair do not address the problem of cationic buildup on the hair shaft.

Liquid crystals have been described as the fourth state of matter and are found in cell membranes as well as diverse inanimate systems, such as "gel-network" emulsions and digital thermometers. Sodium bicarbonate may be incorporated into a cationic emulsion vehicle containing lyotropic liquid crystals. Citric acid may also be incorporated into such an emulsion vehicle. The emulsion containing sodium bicarbonate will form sodium carbonate as it ages and will be alkaline. The liquid crystal dispersion containing citric acid will be strongly acidic. When these two emulsions are combined, "carbonic activation" takes place with the introduction of a carbon dioxide gas phase into an association structure with the liquid crystal gel network.

Conditioning Composition and Method for Removing Chemically Bound Residues and Mineral Deposits from Hair U.S. Pat. No. 6,365,143 issued Apr. 3, 2002 to Hlavac and Lundmark and incorporated herein by reference discloses a cleansing composition and method for removing chemically bound residues and mineral deposits from hair. The inventive compositions include three ingredients: an aminoacetic acid (glycine), a member selected from the group consisting of a salt of ethylenediaminetetraacetic acid, a salt of hydroxyethylethylediaminetriacetic acid, and a salt of diethylenetriaminepentaacetic acid, and mixtures thereof; and citric acid at a weakly alkaline pH. The resultant "citrified sodium glycinate edetate" (CGSE) complex appears to be capable of penetrating into the peripheral region of the hair fiber where absorbed minerals, such as copper and iron, are primarily located. The weakly alkaline environment is advantageous to the promotion of cuticle swelling, thereby enhancing penetration of the chelating complex. When an anionic polysulfonate salt is included in cleansing compositions containing the CGSE complex, the removal of undesirable buildup such as cationic polymer and other cosmetic material on hair fiber surfaces is also facilitated.

An extension of the above technology involves the incorporation of citrified sodium glycinate edetate into a cationic gel-network liquid crystal emulsion vehicle containing sodium bicarbonate. When combined with a secondary vehicle containing a suitable acid (e.g. citric acid) or an acidic polymer (e.g. polyacrylamidomethylpropane sulfonic acid or HSP-1180 available from the Henkel Corporation), carbonic activation takes place with carbon dioxide being liberated, causing the resultant composition to foam. When rinsed from the hair with water, bound minerals (e.g. copper and iron) are removed while the hair is simultaneously conditioned.

If the acidic, strongly anionic polymer HSP 1180 is used as an acidic activator for the bicarbonate/glycinate edetate emulsion complex, cationic buildup problems are often rectified without precipitate formation. This observation appears to be unique in that cationic and anionic substances are typically incompatible and often form gummy precipitates when combined.

What follows is suggested exemplification of the products of the present invention.

EXAMPLE I

A hair conditioner composition is formed by combining a citric acid activator "gel-network" emulsion with a cationic emulsion containing conditioning agents and sodium bicarbonate. After combining parts A and B, the effervescent emulsion is applied to the hair and rinsed out, leaving the hair soft and silky-feeling after drying.

|  | % by weight |
|---|---|
| Activator (Part A) | |
| A. Water | 82.90 |
| Citric Acid | 6.00 |
| Carsoquat SDQ-85 (Stearalkonium Chloride) | 4.00 |
| B. Cetyl Alcohol | 2.80 |
| Arlacel 165 | 1.00 |
| (Glyceryl Stearate and PEG-100 Stearate) | |
| Stearyl Alcohol | 2.00 |
| C. Germaben II (preservative) | 1.00 |
| Fragrance | 0.30 |
|  | 100.00 |
| Conditioner (Part B) | |
| A. Water | 85.28 |
| Panthenol | 0.12 |
| Incroquat Behenyl TMS | |
| (Behentrimonium Methosulfate | 4.00 |
| and Cetearyl Alcohol) | |
| B. Arlacel 165 | 0.50 |
| (Glyceryl Stearate and PEG-100 Stearate) | |
| Promulgen G (Stearyl Alcohol and Ceteareth-20) | 0.40 |
| Cetyl Alcohol | 0.40 |
| Isopropyl Palmitate | 3.00 |
| C. Sodium Bicarbonate | 5.00 |
| D. Germaben II (preservative) | 1.00 |
| E. Fragrance | 0.30 |
|  | 100.00 |

EXAMPLE II

A citrified sodium glycinate edetate (CGSE) complex is formed by dissolving glycine in water, followed by the addition of the tetrasodium salt of ethylenediaminetetraacetic acid and citric acid to a pH of 7.50.

|  | % by weight |
|---|---|
| Distilled water | 90.43 |
| Tetrasodium EDTA (38% solution) | 5.60 |
| Glycine | 3.50 |
| Citric acid | 0.42 |

-continued

| | % by weight |
|---|---|
| Kathon ® CG (Preservative) | 0.05 |
| | 100.00 |

The above CGSE complex was clear and uniform after mixing at 25 C.

EXAMPLE III

A hair conditioner composition is prepared containing CGSE complex. The activator (part A) of Example I is combined with the conditioner (part B) of Example I, which also contains 1.00% of the CSDE complex in the water phase A, shown in Example II.

EXAMPLE IV

A clarifying shampoo is prepared containing the Example II CGSE complex:

| | % by weight |
|---|---|
| Distilled water | 44.00 |
| Sulfochem ® ES2 (Sodium Laureth Sulfate) | 35.00 |
| Lexaine ® C (Cocamidopropyl Betaine) | 7.00 |
| Hamposyl L-30 (Sodium Lauroyl Sarcosinate) | 3.00 |
| DL Panthenol | 0.12 |
| Tetrasodium EDTA (38%) | 5.60 |
| Glycine | 3.50 |
| Citric Acid | 0.42 |
| Sodium Chloride | 1.00 |
| Fragrance | 0.31 |
| Kathon ® CG (preservative) | 0.05 |
| | 100.00 |

The above shampoo is clear and uniform and has a pH of 7.30

EXAMPLE V

A control shampoo is prepared without the Example II CGSE complex:

| | % by weight |
|---|---|
| Distilled water | 53.52 |
| Sulfochem ® ES-2 (Sodium Laureth Sulfate) | 35.00 |
| Lexaine ® C (Cocamidopropyl Betaine) | 7.00 |
| Hamposyl ® L-30 (Sodium Lauroyl Sarcosinate) | 3.00 |
| DL Panthenol | 0.12 |
| Sodium Chloride | 1.00 |
| Fragrance | 0.31 |
| Kathon ® CG | 0.05 |
| | 100.00 |

The above shampoo base is clear and uniform and was adjusted to a pH of 7.30 with citric acid.

EXAMPLE VI

Green Color Copper Removal Test

The phenomenon of blonde hair acquiring a green tint when exposed to swimming pool water containing copper has been attributed to the formation of a weak copper salt complex in the hair shaft. Oxidation of the hair enhances copper absorption. Blonde hair which has been damaged by a perming (permanent waving) process and/or a hydrogen peroxide bleaching process, is especially susceptible to rapid uptake of copper. This causes the damaged blonde hair to take on a green coloration, which cannot be removed by a conventional cleansing and conditioning process.

Damaged blonde hair, which has been permed and bleached, may be soaked in a solution of copper sulfate and sodium hypochlorite bleach to simulate extreme green color uptake conditions in the laboratory. When damaged blonde green hair is soaked in the Example II CGSE complex and rinsed, the green coloration is removed, demonstrating copper mineral complex removal from the hair shaft. When damaged blonde green hair is shampooed with the Example V formula and rinsed, the green coloration remains. When damaged blonde green hair is conditioned with the Example I formula and rinsed, the green coloration remains. When damaged blonde green hair is conditioned with the Example II formula containing CGSE complex and rinsed, the green coloration is removed, demonstrating copper mineral complex removal from the hair shaft. When damaged blonde green hair is shampooed with the Example IV formula containing CGSE complex and rinsed, the green coloration is removed, demonstrating copper mineral complex removal from the hair shaft.

EXAMPLE VII

A hair activator is prepared using an acidic polymeric composition of the type specified in U.S. Pat. No. 4,412,026 issued to Collins Oct. 25, 1983, and in particular, the homopolymeric salt of 2-acrylamido-2-methylpropanesulfonic acid ("HSP 1180").

Activator (Part A) is prepared with 6% active acidic anionic polymer.

| | % by weight |
|---|---|
| Water | 56.00 |
| HSP 1180 | 44.00 |
| | 100.00 |

The above activator is combined with Part B of the conditioner formula shown in Example I, yielding an effervescent emulsion containing anionic polysulfonate polymer.

EXAMPLE VIII

Polymer Buildup Removal Test

Generally, hair acquires an overall negative charge in water. LUMICREASE BORDEAUX 3LR is a negatively charged polyazo sulfonate dye molecule, which is attracted to positively charged sites on hair and adsorbed cationic surfactants and polymers. The greater the dye adsorption, the greater the cationic charge density on the hair fiber surface. Dye adsorption (red-pink coloration) is therefore a function of cationic deposition and substantivity.

A damaged permed and bleached hair tress is soaked in a 1% solution of Polyquatemium-10 (a polymeric quaternary ammonium salt of hydroxyethyl cellulose reacted with a trimethyl ammonium substituted epoxide) to create cationic polymeric deposition on the hair shaft. The tress is then shampooed with 40% active triethanolamine lauryl sulfate solution and rinsed with tap water. The cycle was repeated five times.

Hair fibers from the polymer buildup tress were then treated with the effervescent emulsion containing polysulfonate polymer (shown in Example VII), followed by rinsing in tap water. The hair fibers yield a negative Lumicrease dye test result (no red-pink coloration) which indicates that the cationic polymeric buildup has been removed.

Hair fibers from the cationic polymeric buildup tress which were treated with effervescent emulsion containing no polysulfonate polymer (Example I) yielded a positive red LUMICREASE dye test result which indicates the presence of cationic polymeric buildup on the hair shaft.

EXAMPLE IX

An alpha-hydroxy acid skin cream composition is formed by combining a lactic acid activator gel with a behentrimonium methosulfate "gel-network" emulsion containing sodium bicarbonate. After combining parts A and B, the effervescent emulsion is applied to the skin for anti-aging effects.

|   |   | % by weight |
|---|---|---|
| Activator Gel (Part A) | | |
| A. | Water | 85.45 |
|  | Xanthan Gum | 0.75 |
|  | Covera ® (Aloe Barbadensis Leaf Juice) | 0.30 |
| B. | Water | 10.00 |
|  | Lactic Acid | 2.50 |
| C. | Germaben II (preservative) | 1.00 |
|  |  | 100.00 |
| "Gel-Network" Emulsion Base (Part B) | | |
| A. | Emulsifying Wax (Stearyl Alcohol and Ceteareth-20) | 10.00 |
|  | Incroquat ® Behenyl TMS (Behentrimonium Methosulfate and Cetearyl Alcohol) | 3.00 |
|  | Mineral oil | 5.00 |
| B. | Sodium Bicarbonate | 5.00 |
| C. | Water | 75.88 |
| D. | Germaben II (preservative) | 1.00 |
| E. | Fragrance | 0.12 |
|  |  | 100.00 |

After activation (Part A+Part B), liquid-crystal gel network structures encapsulate carbon dioxide gas bubbles facilitating penetration of Aloe and alpha hydroxy acid into the stratum corneum skin surface.

Conditioning Composition and Method for Delivering Active Ingredients to Skin and Hair After the addition of an acidic composition to a gel-network emulsion containing sodium bicarbonate, carbon dioxide gas bubbles are generated in the form of a heterogeneous gas-in-emulsion dispersion.

Immediately after activation, gel-network interaction with the generated gas phase tends to form stabilized liquid crystal gas globules that can be formulated to contain active ingredients for delivery to skin and hair. With the passage of time, large gas bubbles and smaller bubbles which have not been stabilized will coalesce and dissipate from the dispersion. What is left behind, is a gel-network dispersion containing encapsulated microscopic gas bubbles that can facilitate transdermal delivery of active ingredients to skin and deliver functional ingredients to the hair.

A gel-network liquid crystal emulsion with encapsulated gas phase microglobules is prepared which after aging 24 hours at room temperature retains microscopic gas bubbles in the gel-network.

Cosmetic Hair Care Compositions

When the inventive composition is a hair care composition, it acts as a delivery vehicle for active substances that can facilitate bound minerals and cationic polymer removal. The emulsions of the present invention may also be used to deliver active substances into the hair shaft for the purpose of conditioning and cuticle repair.

Surfactant materials are selected from nonionic, amphoteric, anionic or cationic surfactants or mixtures thereof. Such hair conditioning products preferably comprise one or more cationic surfactants. The use of cabonic surfactants is especially preferred, because these ingredients are capable of providing conditioning benefits to hair and favor the formation of liquid crystal gel networks, when used in combination with appropriate fatty amphiphiles and water. Appropriate fatty amphiphiles include fatty alcohols, such as cetyl, stearyl, and cetearyl.

An example of a cationic/fatty amphiphiphile combination which favors the formation of liquid crystal gel-networks is behentrimonium methosulfate and cetearyl alcohol.

Cosmetic Skin Care Compositions

The preferred cosmetic skin care compositions according to the present invention are products for the treatment of skin aiming to achieve anti-aging benefits. Such compositions preferably include a sunscreen to further minimize aging which results from exposure of skin to harmful UV-A and UV-B rays.

An oil or oily material may be present, together with an emulsifier and an appropriate fatty amphiphile which favors the formation of liquid crystal gel-networks. Suitable fatty amphiphiles include fatty alcohols and acids having from 10 to 20 carbon atoms. Especially preferred are compounds such as cetyl, myristyl, and stearyl alcohols, and stearic acid and palmitic acid.

Emollients are often incorporated into compositions of the present invention. Levels of such emollients may range from 0.5% to 50%, preferably between 5% and 10% by weight of the total composition. Emollients may be classified under such general chemical categories as fatty acids, esters, fatty alcohols, polyols and hydrocarbons.

Another category of functional ingredients within the cosmetic skin care compositions of the present invention are thickeners. A thickener will usually be present in amounts anywhere from 0.1% to 10% by weight, preferably from about 0.5% to 1% by weight of the composition.

Active ingredients with anti-aging benefits include alpha hydroxy acids, such as glycolic acid and lactic acid. Botanical extracts with known beneficial effects on the skin, include Aloe Barbadensis leaf juice. Such botanical active ingredients are desired components of the emulsions of the present invention skin care compositions.

Ascorbic acid (vitamin C) and Magnesium Ascorbyl Phosphate may also be used in the emulsions of the present invention for their known antioxidant benefits. Skin care compositions may also include other minor components, such as coloring agents, opacifiers and fragrances.

A second aspect of the present invention relates to a composition and method for removing chemically bound minerals from hair comprising a multidentate ligand complex and water in a weakly alkaline environment. The complex is formed by adding glycine to an alkaline solution of a member selected from the group consisting of a salt of ethylenediaminetetraacetic acid, a salt of hydroxyethylethylenediaminetriacetic acid, and a salt of diethylenetriaminepentaacetic acid, and mixtures thereof. Preferably, the salt is the tetrasodium salt of ethylenediaminetetraacetic acid (EDTA) followed by the addition of citric acid to a weakly alkaline pH of approximately 7.5. The resultant "citrified glycine edetate" composition has been found to be highly effective in removing bound environmental minerals by a unique hair penetration and chelation process. It is understood that while citric acid is the preferred ingredient, that any material capable of generating citric acid is included within the definition of citric acid. Thus, citrate salts such as sodium citrate may be employed herein.

Chelation is a chemical reaction or process involving chelate ring formation and is characterized by multiple bonding between two or more of the electron-pair-donor groups of a multidentate ligand and electron-pair-acceptor metal ion.

It is an object of the present invention to provide a synergistic composition suitable for removing minerals from hair, which includes the tetrasodium salt of amino acetic acid (glycine), and the tetrasodium salt of ethylenediaminetetraacetic acid neutralized to a weakly alkaline pH with citric acid.

It is another object of the present invention to provide a process for simultaneously removing minerals and cationic surfactant and/or polymer buildup with a composition containing the tetrasodium salt of amino acetic acid and the tetrasodium salt of ethylenediaminetetraacetic acid neutralized to a weakly alkaline pH with an anionic polymer such as polyacrylamidomethylpropane sulfonic acid. It is theorized that the sulfonic acid portion of the polymer molecule and amino acetic acid forms hydrogen bonds with the tetrasodium salt of ethylenediaminetetraacetic acid forming a polyglycine edetate complex.

Hair is an assembly of fibers that contain proteins, which may bind minerals by both ionic bonds and covalent bonds. Cationic surfactants and polymers are positively charged molecules, which have an affinity for negatively charged sites on the hair. Undesirable buildup on hair fiber surfaces may result when certain types of cationic surfactants and polymers are used repeatedly to condition the hair.

The inventive compositions include three ingredients: aminoacetic acid (glycine), a member selected from the group consisting of a salt of ethylenediaminetetraacetic acid, a salt of hydroxyethylethylenediaminetriacetic acid, and a salt of diethylenetriaminepentaacetic acid, and mixtures thereof; and citric acid at a weakly alkaline pH. The resultant "citrified sodium glycinate edetate" complex appears to be capable of penetrating into the peripheral region of the hair fiber where absorbed minerals, such as copper, are primarily located. The weakly alkaline environment is advantageous to the promotion of cuticle swelling, thereby enhancing penetration of the chelating complex.

The inventive composition is preferably applied to the hair as a spray followed by shampooing for mineral removal. An alternative approach is to incorporate the glycinated chelating complex directly into a shampoo or hair conditioner for mineral removal. When an anionic polysulfonate salt is included in cleansing compositions containing the glycinated-chelating complex, the removal of undesirable buildup on hair fiber surfaces is also facilitated.

EXAMPLE X

An environmental minerals hair clarifying spray is prepared containing citrified sodium glycinate edetate (CGSE) complex and the anionic polymer, sodium polystyrene sulfonate (Flexan® 130):

|  | % by weight |
| --- | --- |
| Water | 84.80 |
| DL Panthenol | 0.12 |
| Flexan ® 130 (Sodium Polystyrene Sulfonate) | 3.33 |
| Glycine | 3.50 |
| Tetrasodium EDTA (38%) | 5.60 |
| Citric Acid | 0.40 |
| Fragrance | 0.25 |
| ARLSOLVE ® 200L (Isoceteth-20) | 1.00 |
| Germaben II ® (preservative) | 1.00 |
|  | 100.00 |

The above clarifying spray is clear and uniform and is water-thin, suitable for spraying as a mist.

EXAMPLE XI

Damaged green hair, described earlier, is sprayed with the composition shown in Example X. After the shampooing and rinsing with the control shampoo without CGSE complex (formula shown in Example V), the green color is removed. The clarifying spray can therefore be used as a pretreatment on green hair to facilitate copper complex removal by using conventional shampoos which do not contain the CGSE complex.

EXAMPLE XII

Cationic Polymer Buildup Removal Test

Generally, hair acquires an overall negatively charge in water. LUMICREASE BORDEAUX 3LR is a negatively charged polyazo sulfonate dye molecule, which is attracted to positively charged sites on hair and adsorbed cationic surfactants and polymers. The greater the dye adsorption, the greater the cationic charge density on the hair fiber surface. Dye adsorption (red-pink coloration) is therefore a function of cationic deposition and substantivity.

A damaged permed and bleached hair tress is soaked in a 1% solution of Polyquaternium-10 ® (a polymeric quaternary ammonium salt of hydroxyethyl cellulose reacted with a trimethyl ammonium substituted epoxide) to build up a cationic polymeric deposition upon the hair. The tress is then washed with the control shampoo Example V. composition, which did not contain CGSE complex or anionic polysulfonate polymer. The cycle was repeated five times. Hair fibers from the cationic polymeric buildup tress yield a positive red Lumicrease dye test result which indicates cationic polymeric buildup on the hair shaft.

Hair fibers from the cationic polymeric buildup tress were sprayed with the clarifying mist formula shown in Example X followed by washing with the control shampoo composition shown in Example V. The hair fibers yield a negative Lumicrease dye test result (no red-pink coloration) which indicates that the cationic polymeric buildup has been removed.

EXAMPLE XIII

Iron Removal Test

The presence of iron in the hair shaft may be observed with the aid of a light microscope and special staining techniques.

Damaged permed/bleached hair is especially prone to the uptake of iron. This may be demonstrated in the laboratory using hair which has been soaked in a solution of ferric chloride, followed by rinsing, staining and observations with a suitable light microscope.

Damaged permed/bleached hair fibers are soaked in 2% ferric chloride, rinsed and stained with 0.1 M potassium thiocyanate solution. A blood red iron complex forms which may be observed with a suitable light microscope.

The presence of iron in the hair shaft may also be visualized using light microscopy and a potassium ferrocyanide staining technique. Iron (ferric ion) forms a dark-blue complex in the presence of potassium ferrocyanide.

Damaged permed/bleached hair fibers are soaked in 2% ferric chloride followed by shampooing and rinsing, using the clarifying shampoo composition shown in Example IV. The absence of a dark-blue color after uptake of 0.1M potassium ferrocyanide solution indicates that the clarifying shampoo facilitates iron removal from hair.

Amounts of the Components

The compositions of the present invention contain the amino acetic acid, preferably glycine, at a concentration of 1.0 percent to about 5.0 percent by weight of the total composition. Preferably, the concentration of the amino acetic acid in the composition is from about 1.1 percent to about 4.0 percent by weight of the total composition.

The compositions of the present invention contain water at a concentration of about 10 percent to about 85 percent by weight of the total composition. Preferably, the concentration of the water is about 15 percent to about 80 percent by weight of the total composition.

The compositions of the present invention contain citric acid at a concentration of about 1.0 percent to about 15 percent by weight of the total composition. Preferably, the concentration of the citric acid, as citric acid, is about 1.2 percent to about 13 percent by weight of the total composition.

The amount of water-soluble source of bicarbonate in the formulation is about 1 percent to about 30 percent by percent by weight, preferably about 3 to about 10 percent by weight. The amount of panthenol in the formulation is from about 0.01 to about 5 percent by weight, preferably about 0.05% to about 2.5 percent by weight. The citric acid is present at about 2 percent to about 20 percent by weight.

The compositions of the present invention have an alkaline pH. Preferably, the pH is about is about 7.01 to about 8.5, more preferably 7.1 to about 8.2

Composition Preparation

The composition is prepared by combining the various ingredients in a suitable mixing vessel. The mixing is continued for about one half-hour. Preservatives and fragrances should be added to the composition at temperatures of 45 C. or less. Any remaining ingredients may be added at any point in the process where the added ingredient maintains its intended function and where the added ingredient does not interfere with the remainder of the composition.

Composition Utilization

For the best results it is suggested that the hair be wet when the composition is applied. The compositions of the present invention may be formulated into lotions, balms, and mousses or hair conditioners and the like. The level of usage in the finished products for consumer use is typically to apply the product at 0.1 grams to 50 grams per liter of liquid composition applied or directly upon the hair at 0.1 gram to 1 gram per 250 grams of hair. The products containing the compositions of the present invention is conveniently applied to the hair at room temperature to slightly elevated temperatures, e.g. 18 to 38 degrees Celsius.

Optional Ingredients

The products containing the compositions described herein can contain a variety of nonessential optional components suitable for rendering such compositions more cosmetically acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea.

Additional ingredients include thickeners and viscosity modifiers such as a diethanolamide of a long chain fatty acid (e.g., PEG 3 Lauramide DEA) cocomono-ethanolamide, amine oxides, block polymers of ethylene oxide and propylene oxide such as Pluronic F88 offered by BASF Wyandotte, fatty alcohols such as cetearyl alcohol, sodium chloride, sodium sulfate, polyvinyl alcohol, and ethyl alcohol; pH adjusting agents such as citric acid, sodium citrate, succinic acid, phosphoric acid, sodium hydroxide, sodium carbonate, etc., perfumes; dyes; and, sequestering agents. Such agents generally are used individually at a level of from about 0.01% to about 10%, preferably from about 0.5% to about 5.0% by weight of the composition.

What is claimed is:

1. A composition suitable for conditioning a keratinous substrate comprising:
   (a) panthenol;
   (b) citric acid;
   (c) water; and,
   a water-soluble source of bicarbonate
   wherein the composition is a liquid crystal.

2. The composition of claim 1 further comprising a member selected from the group consisting of a salt of ethylenediaminetetraacetic acid, a salt of hydroxyethylethylenediaminetriacetic acid, and a salt of diethylenetriaminepentaacetic acid, and mixtures thereof.

3. The composition of claim 1 wherein:
   (a) the panthenol is present at about 0.01 percent to about 5 percent by weight;
   (b) the citric acid is present at about 1 percent to about 25 percent by weight;
   (c) the water is present at about 50 percent to about 95 percent by weight; and,
   (d) the water-soluble source of bicarbonate is present at about 1 percent to about 30 percent by weight.

4. The composition of claim 1 wherein the water-soluble source of bicarbonate is sodium bicarbonate.

5. The composition of claim 1 wherein:
   (a) the panthenol is present at about 1 percent to about 10 percent by weight;
   (b) the citric acid is present at about 2 percent to about 20 percent by weight;
   (c) the water is present at about 50 percent to about 90 percent by weight; and,
   (d) the water-soluble source of bicarbonate is present at about 1 percent to about 30 percent by weight.

6. The composition of claim 1 further comprising an aminoacetic acid.

7. The composition of claim 1 wherein the aminoacetic acid is glycine.

8. A method of treating a keratinous substrate by applying simultaneously an effective amount of both parts of a two part liquid composition to a keratinous substrate wherein the two part composition comprises:
   (a) a first mixture comprising water and citric acid; and,
   (b) a second mixture comprising panthenol and, a water-soluble source of bicarbonate.

9. The method of claim 8 further comprising a member selected from the group consisting of a salt of ethylenediaminetetraacetic acid, a salt of hydroxyethylethylediaminetriacetic acid, and a salt of diethylenetriaminepentaacetic acid, and mixtures thereof in one of mixture (a) or mixture (b).

10. The method of claim 8 wherein the water and the citric acid in the first mixture are present in a respective weight ratio of about 40:1 to about 10:1.

11. The method of claim 8 wherein the panthenol and the water-soluble source of bicarbonate in the second mixture are present in a respective weight ratio of about 20:1 to about 1:10.

12. The method of claim 8 further comprising an aminoacetic acid in one of mixture (a) or mixture (b).

13. The method of claim 12 wherein the aminoacetic acid is glycine.

14. A composition suitable for conditioning a keratinous substrate comprising:
   (a) panthenol;
   (b) citric acid;
   (c) water;
   (d) a water-soluble source of bicarbonate; and,
   (e) a member selected from the group consisting of a water-insoluble linear alcohol and a fatty acid ester and mixtures thereof
wherein the composition is a liquid crystal.

15. The composition according to claim 14 wherein:
   the panthenol is present at about 1 percent to about 10 percent by weight;
   the citric acid is present at about 2 percent to about 20 percent by weight;
   the water is present at about 50 percent to about 90 percent by weight;
   the water-soluble source of bicarbonate is present at about 1 percent to about 30 percent by weight and,
   the member selected from the group consisting of a water-insoluble linear alcohol and a fatty add ester and mixtures thereof is present at about 0.25 percent about 20 percent by weight.

16. A composition suitable for conditioning a keratinous substrate comprising:
   a. panthenol;
   b. citric acid;
   c. water;
   d. a water-soluble source of bicarbonate; and,
   e. a quaternary compound
wherein the composition is a liquid crystal.

17. The composition according to claim 16 wherein:
   the panthenol is present at about 1 percent to about 10 percent by weight;
   the citric acid is present at about 2 percent to about 20 percent by weight;
   the water is present at about 50 percent to about 90 percent by weight;
   the water-soluble source of bicarbonate is present at about 1 percent to about 30 percent by weight and,
   the quaternary compound is present at about 0.5 percent to about 20 percent by weight.

18. A composition suitable for conditioning a keratinous substrate comprising:
   water,
   a source of a homopolymeric salt of 2-acrylamido-2-methylpropanesulfonic acid;
   panthenol; and,
   a water-soluble source of bicarbonate.

19. The composition according to claim 18 wherein the water and the source of a homopolymeric salt of 2-acrylamido-2-methyl-propanesulfonic acid are present in a respective weight ratio of about 40:1 to about 10:1.

20. The composition of claim 18 wherein the panthenol and the water-soluble source of bicarbonate are present in a respective weight ratio of about 20:1 to about 1:10.

21. A two part composition suitable for conditioning a keratinous substrate comprising:
   (a) a first mixture comprising water and a source of a fruit acid other than citric acid and,
   (b) a second mixture comprising panthenol; water; and, a water-soluble source of bicarbonate.

22. The composition of claim 21 additionally comprising an emulsifier.

23. The composition, of claim 21 in the form of an emulsion.

* * * * *